United States Patent [19]

Bugianesi et al.

[11] Patent Number: 4,761,404

[45] Date of Patent: Aug. 2, 1988

[54] PHOSPHOLIPID ANALOGS USEFUL AS PAF SYNTHESIS INHIBITORS

[75] Inventors: Robert L. Bugianesi, Colonia; Mitree M. Ponpipom, Branchburg; Kathleen M. Rupprecht, Cranford, all of N.J.

[73] Assignee: Merck & Co., Inc., Rahway, N.J.

[21] Appl. No.: 750,435

[22] Filed: Jul. 1, 1985

[51] Int. Cl.$^4$ .................. A61K 31/685; C07F 9/10
[52] U.S. Cl. .................................. 514/77; 260/403
[58] Field of Search .......................... 260/403; 514/77

[56] References Cited

U.S. PATENT DOCUMENTS 3,985,875 10/1976 Hayashi et al. .................. 260/403
4,221,732 9/1980 Oette et al. ..................... 260/403

OTHER PUBLICATIONS

Chandrakumar et al., "Biochimica et Biophysica Acta", vol. 711, (1982), pp. 357–360.

Primary Examiner—Anton H. Sutto
Attorney, Agent, or Firm—Theresa Y. Cheng; Michael C. Sudol

[57] ABSTRACT

There are disclosed phospholipid analogs which are useful as PAF synthesis inhibitors. These compounds inhibit PAF (platelet-activating factor) biosynthesis and are thereby useful in the treatment of various diseases or disorders mediated by the PAF such as, for example, pain, fever, inflammation, cardiovascular disorder, asthma, lung edema, allergic disorders, skin diseases, psoriasis, and adult respiratory distress syndrome.

12 Claims, No Drawings

PHOSPHOLIPID ANALOGS USEFUL AS PAF SYNTHESIS INHIBITORS

BACKGROUND OF THE INVENTION

Platelet-activating factor (PAF) has been identified as an acetyl glyceryl ether phosphorylcholine (AGEPC), i.e., 1-O-hexadecyl/octadecyl-2-O-acetyl-sn-glycerol-3-phosphorylcholine [Hanahan, D. S. et al., *J. Biol. Chem.*, 255:5514, (1980)]. Even before its chemical identification, PAF was linked to various biologic activities and pathways making it one of the important mediators responsible for a variety of physiological processes including activation or coagulation of platelets, pathogenesis of immune complex deposition, smooth muscle contraction and inflammation as well as respiratory, cardiovascular and intravascular alterations. These physiological processes are known to be associated with a large group of diseases such as, for example, inflammatory diseases, cardiovascular disorders, asthma, lung edema, and adult respiratory distress syndrome.

The preparation of phosphorylcholines as intermediates for obtaining amide analogs of PAF and related derivatives has been disclosed by M. M. Ponpipom, et al. [*Chemistry and Physics of Lipids*, 35, 29–37 (1984), Elsevier Scientific Publishers Ireland, Ltd.] and N. S. Chandrakumar, et al. [*Biochemecia et Biophysicia Acta*, 711, 357–360 (1982)] disclose the preparation of N-acylaminoethylphosphorylcholines which are stated to function as reversible phospholipase $A_2$ inhibitors.

DESCRIPTION OF THE INVENTION

The present invention is directed at phospholipid compounds and their preparations. These compounds have been found to inhibit platelet-activating factor (PAF) biosynthesis and are therefore useful in the treatment of various disorders or diseases mediated by the PAF such as, for example, pain, fever, inflammation, cardiovascular disorder, asthma, lung edema, allergies, skin diseases, psoriasis, adult respiratory distress syndrome, and the like.

The compounds of the invention are those having the formulae:

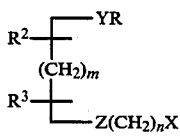   I wherein:
Y represents
  (a) —O;
  (b) —NHCO;
  (c) —NHCOO;
  (d) —NHSOO;
  (e) —NHCONH;
R represents saturated or unsaturated $C_{12}$–$C_{20}$ alkyl;
Y and R together represent —HNCOR$^1$ wherein R$^1$ is:
  (1) substituted saturated or unsaturated $C_1$–$C_4$-alkyl wherein the substitutents are $C_5$ to $C_{10}$ aryl or $C_5$ to $C_{10}$ heteroaryl containing an O, N or S heteroatom;
  (2) substituted $C_5$ to $C_{10}$ aryl wherein the substituent is $C_1$–$C_4$-alkyl;
  (3) $C_5$ to $C_{10}$ heteroaryl containing an O, N or S heteroatom;

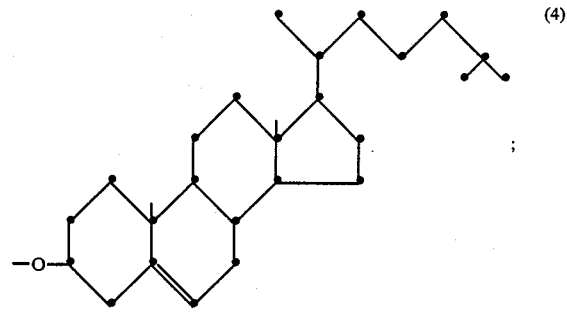

Z represents

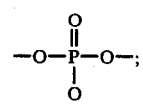 (a)

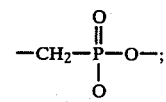 (b)

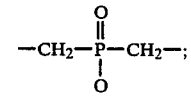 (c)

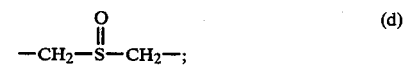 (d)

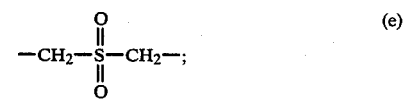 (e)

X is
  (a) trimethylamine:
  (b) alkoxy;
  (c) alkoxycarbonylamino;
  (d) $C_1$–$C_4$ alkylacarbamoylamino;
  (e) substituted $C_1$–$C_4$alkyl-, carbamoylamino wherein the substituent is $C_6$ aryl or a 5- or 6-membered heteroaryl containing 1 to 2 O, N or S heteroatoms;
  (f) hydroxy;
  (g) $C_1$–$C_4$alkyl carbonyl;
  (h) sulfur;
  (i) $C_1$–$C_4$sulfoxide;
  (j) $C_1$–$C_4$alkyl sulfonyl;
  (k) fluoro;
  (l) azido;
  (m) amino;
  (n) acylamino;
  (o) cyano;
  (p) heterocycle having up to 8 ring members, 4 to 7 of which are carbon atoms and containing 1 to 2 O, N or S heteroatoms;

$R^2$ and $R^3$ can each be present or absent and, when present, can be the same or different and are independently
  (a) hydrogen;
  (b) hydroxy;
  (c) unsaturated or saturated, unsubstituted or substituted $C_1$–$C_4$ alkyl group wherein the substituents are hydroxy, acetyl, sulfhydryl, fluoro;

(d) azido;
(e) amido;
(f) acetamido; or,
(g) when R² is present and Y is

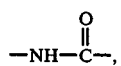

R² can be joined with the NH group and its adjacent C atom to form a 5-, 6- or 7-membered ring containing said N atom;
m is 0–4;
n is 2–6.

Preferred Formula I compounds are those having the formulae:

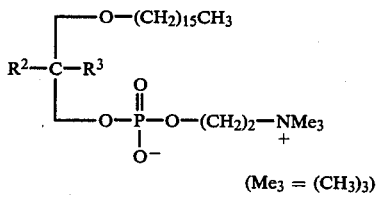

Ia $(Me_3 = (CH_3)_3)$ wherein R² and R³ are as tabulated below:

| R² | R³ |
|---|---|
| H | F |
| H | H |
| CH₂F | H |
| CH₂= | |
| CH₂OH | H |
| CH₂OH | OH |
| CH₂OAc | H |
| CH₂OAc | OH |
| CH₃ | OH |
| H | N₃ |
| H | NH₂ |
| H | NHAc |

(OAc = acetate)

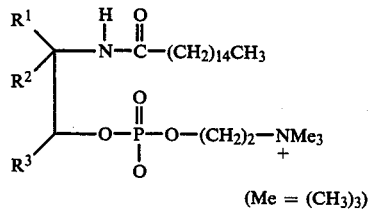

Ib $(Me = (CH_3)_3)$ wherein R¹, R² and R³ are as tabulated below:

| R¹ | R² | R³ |
|---|---|---|
| H | H | H |
| H | H | CH₂CH₃ |
| CH₃ | CH₃ | H |
| CH₃ | H | H |
| CH₂CH₃ | H | H |

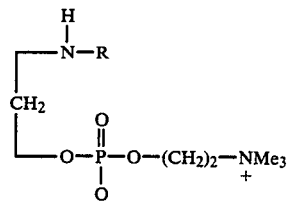

Ic $(Me = (CH_3)_3)$ wherein:
R is —CO(CH₂)₁₄CH₃;
—COO(CH₂)₁₃CH₃;
—CONH(CH₂)₁₇CH₃; and,
—SO₂(CH₂)₁₅CH₃.

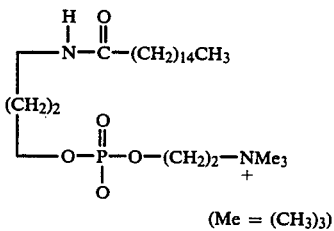

Id $(Me = (CH_3)_3)$

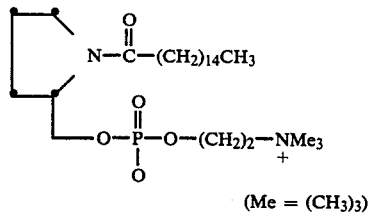

Ie $(Me = (CH_3)_3)$

Some of the end compounds of the invention can be used as starting compounds or intermediates to make other end compounds of the invention. Other compounds used as intermediates to make end compounds of the invention are similar to but not the same as the end compounds of the invention. These compounds are useful intermediates and are believed to be novel. These novel intermediates, therefore, have the same general structure as the Formula I compounds wherein R, R², R³, Z, Y and R together, m and n are as defined above for Formula I, Y is the same as defined for Formula I but also includes —NH₂ and X is I.

Utility of the Compounds of the Invention

This invention also relates to a method of treatment for human patients (or mammalian animals raised in the diary, meat, or fur industries or as pets) suffering from disorders or diseases which can be attributed to PAF as previously described and, more specifically, a method of treatment involving the administration of a compound of the invention as the active constituent.

Accordingly, the compounds of the invention can be used, among other things, to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, a compound of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use such as, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

A compound of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing a compound of the invention are employed.

Dosage levels of the order from about 1 mg to about 100 mg per kilogram of body weight per day of a compound of the invention are useful in the treatment of the above-indicated conditions (from about 50 mg to about 5 gms. per patient per day). For example, inflammation is effectively treated and anti-pyretic and analgesic activity manifested by the administration from about 25 to about 75 mg of the active compound per kilogram of body weight per day (about 75 mg to about 3.75 gms per patient per day). Advantageously, from about 5 mg to about 50 mg per kilogram of body weight per daily dosage produces highly effective results (about 250 mg to about 2.5 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active compound with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Reaction Schemes and Examples serve to illustrate but are not intended to limit the scope of the present invention.

REACTION SCHEME I, EXAMPLES 1-18

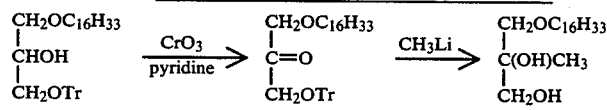
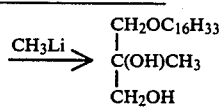
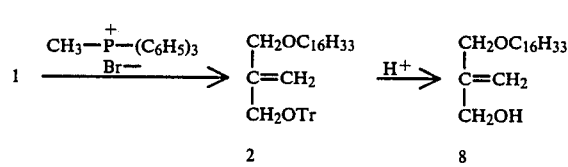
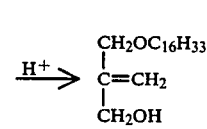
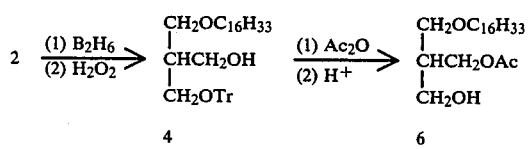
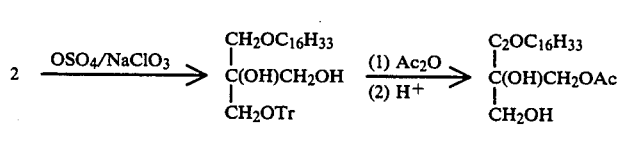
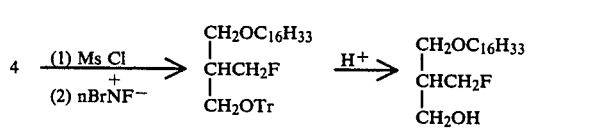

REACTION SCHEME I, EXAMPLES 1-18 -continued

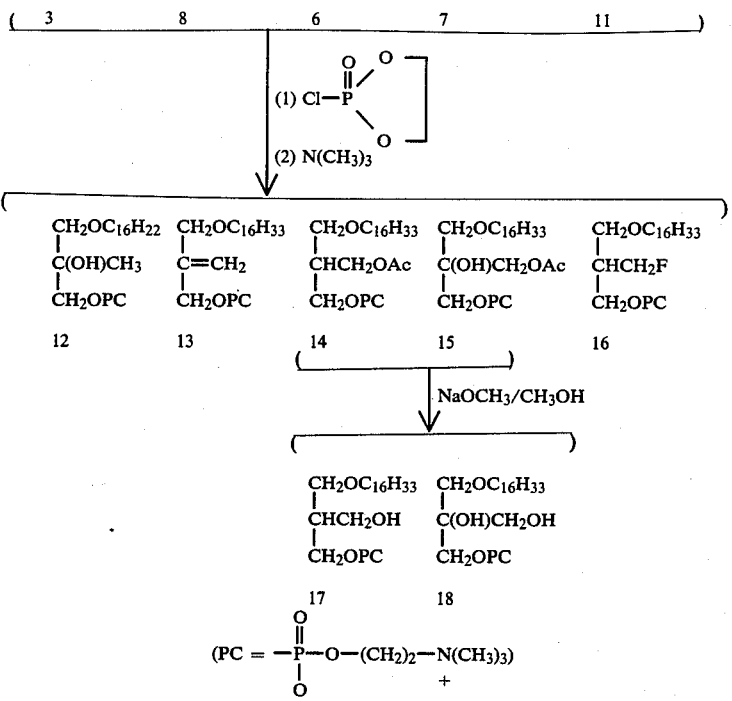

EXAMPLE 1

1-Hexadecyloxy-3-triphenylmethoxypropan-2-one (1)

A soluton of pyridine (204 ml, 2.53 mol) in anhydrous $CH_2Cl_2$ (2.5 l) was cooled to 0° and to this was added $CrO_3$ (1.76 g, 1.74 mol) in 10 portions. The mixture was stirred at 0° for 90 minutes and crude racemic 1-0-hexadecyl-3-0-triphenylmethylglycerol (a) (178.4 g, 0.319 mol) was added. The mixture was warmed to room temperature and stirred under $N_2$ for 4 hours. Then $CrO_3$ (32.0 g, 0.316 mol) and pyridine (60 ml, 0.744 mol) were added and the mixture was stirred at room temperature overnight.

The solution was decanted into ice water-$NaHCO_3$ and the sludgy residue was extracted with ether and decanted. The layers were separated and the organic layer was washed with water, dried over $Na_2SO_4$, and concentrated. The residue was purified by HPLC (silica gel, 5% ethyl acetatehexane) and crystallized from ethanol to afford 126 g (71%) of the title compound (1) as white needles, m.p. 38°. NMR (CDC13, $(CH_3)_4Si$); δ0.90 (m, $-CH_3$), 1.29 (s, br, $-CH_2-$), 1.60 (m, $-OCH_2CH_2R$), 3.47 (m, $OCH_2R$), 3.96 (d, J=4.5 Hz, $CH_2OTr$), 4.35 (d, J=4.5 Hz, $CH_2OR$), 7.2-7.5 (m, $C(C_5HHD 5)_3$).

EXAMPLE 2

3-Hexadecyloxy-3-(triphenylmethoxymethyl)-1-propene (2)

A solution of n-butyllithium (47 ml, 113 mmol) in hexane was added to a suspension of methyltriphenylphosphonium bromide (40.0 g, 112 mmol) in 100 ml dry dioxane under $N_2$ and the dark red solution was stirred at room temperature for 45 minutes. Compound 1 (35.1 g, 63.1 mmol) in 100 ml dry dioxane was added and the mixture was stirred for 2 hours. Water (10 ml) was added and the solution was partitioned between hexane and water. The aqueous layer was washed 2 times with hexane and the combined organic layers were dried over $Na_2SO_4$ and concentrated. The residue was crystallized from ethanol to afford 28.8 g (82%) of the title compound (2) as white needles, m.p. 34° ; NMR (CDCl$_3$, $(CH_3)_4Si$); δ0.90 (t, 3H, J=6 Hz, $-CH_3$), 1.25 (s, 26H, $-CH_2-$), 1.62 (m, 2H, $-OCH_2CH_2R$), 3.35 (t, 2H, J=7 Hz, $-OCH_2R$), 3.62 (s, 2H, $CH_2\overline{O}Tr$), 3.96 (s, 2H, $-CH_2OR$), 5.$\overline{20}$ (d, 1 H, J=2 Hz, olefin), 5.40 (d, 1H, J=$\overline{2}$ Hz, olefin), 7.2-7.5 (m, 15H, $C(C_6\underline{H}_5)85)_3$).

EXAMPLE 3

1-O-Hexadecyl-2-methylglycerol (3)

A solution of methyllithium (5.0 ml, 7.50 mmol) in hexane was added to a solution of (2.00 g, 3.59 mmol) in 10 ml dry dioxane. After 2 hours, 2-propanol (1 ml) was added dropwise and the solution was concentrated. The residue was dissolved in 4:3:1 glacial acetic acid-ethanol-water (10 ml), and the solution was heated on a steam bath for 2 hours and concentrated. Chromatography on silica gel using 20% ethylacetatehexane and crystallization from hexane afforded 0.738 g (62%) of the title compound (3) as white needles, m.p. 56°. NMR (CDCl$_3$, $(CH_3)_4Si$); δ0.90 (t, 3H, J=6 Hz, $-CH_3$), 1.07 (s, 3H, $-CH_3$), 1.25 (s, 26H, $-CH_2-$), 1.59 (m, 2H, $-OCH_2CH_2R$), 2.51 (d of d, 1H, /$J_{AX}$/=4.5 Hz, /$J_{BX}$/=8.$\overline{5}$ Hz, $-O\underline{H}$), 2.86 (s, 1$\overline{H}$, $-OH$), 3.38, 3.50 (AB, 2H, $J_{AB}$=10.5, $\overline{CH_2}OR$), 3.48 (t, 2$\overline{H}$, J=6.5 Hz, $-OC\underline{H}2R$), 3.46, 3.68 $\overline{(A}BX$, 2H, $J_{AB}$=11, C$\underline{H_2}$-OH).

EXAMPLE 4

3-Hexadecyloxy-2-triphenylmethoxymethylpropan-1-ol (4)

A solution of compound 2 (5.00 g, 9.01 mmol) in 10 ml dry dioxane and $BH_3$-tetrahydrofuran (10 ml, 10.0 mmol) in tetrahydrofuran was stirred at room temperature for 2 hours. Water (10 ml) was added dropwise, followed by 2.5 N NaOH (20 ml) and 30% H$_2$O$_2$ (7.5 ml). The mixture was stirred at 50° for 2.5 hours, then was cooled and partitioned between CH$_2$Cl$_2$ and water. The aqueous layer was washed 3 times with CH$_2$Cl$_2$ and the combined extracts were dried over Na$_2$SO$_4$ and concentrated. Chromatography on silica gel using 10% ethyl acetatehexane afforded 3.37 g (66%) of the title compound (4) as a waxy white solid, m.p. 38°. NMR (CDCl$_3$, (CH$_3$)$_4$Si); δ0.90 (t, 3H, J=6 Hz, —CH$_3$), 1.25 (s, 26H, —CH$_2$—), 1.54 (m, 2H, —OCH$_2$CH$_2$R), 2.16 (m, 1H, CH), 2.70 (t, 1H, J=6.5 Hz, —OH), 3.22 (d, 2H, J=6 Hz, CH$_2$OTr), 3.41 (t, 2H, J=6 Hz, —OCH$_2$R), 3.61 (t, 2H, J=6 Hz, CH$_2$OR), 3.77 (t, 2H, J=6.5 Hz, CH$_2$OH), 7.2-7.52 (m, 15H, C(C$_6$H$_5$)$_3$).

EXAMPLE 5

1-Hexadecyl-2-triphenylmethoxymethylglycerol (5)

A mixture of compound 2 (4.10 g, 7.39 mmol), OsO$_4$ (0.50 g, 2.00 mmol), and NaClO$_3$ (2.10 g, 17.1 mmol) in 80% aqueous tetrahydrofuran was stirred at room temperature for 2 hours. The solution was partitioned between CH$_2$Cl$_2$ and water and the aqueous layer was washed with CH$_2$Cl$_2$. The combined organic washes were concentrated and the residue was dissolved in ethanol. The solution was shaken with NaHSO$_3$ (7.50 g, 69.8 mmol) until all brown material had precipitated. The solution was filtered, concentrated and partitioned between hexane and water. The hexane solution was dried over Na$_2$SO$_4$ and concentrated to a colorless oil that crystallized spontaneously to afford 4.00 g (92%) of the title compound (5) as a waxy white solid, m.p. 38°. NMR (CDCL$_3$, (CH$_3$)$_4$Si); δ0.90 (t, 3H, J=6 Hz, —CH$_3$), 1.25 (s, 26H, —CH$_2$—), 1.56 (m, 2H, —OCH$_2$CH$_2$R), 2.28 (t, 1H, J=7 Hz, —OH), 2.82 (s, 1H, —OH), 4.93, 5.03 (AB, 2H, J=9, CH$_2$OTr), 3.45 (t, 2H, J=6.5 Hz, —OCH$_2$R), 3.58 (s, 2H, CH$_2$OR), 3.65, 3.68 (ABX, 2H, J$_{AB}$=11.5 Hz, /J$_{AX}$/=6.5 Hz, /J$_{BX}$/=6.5 Hz, —CH$_2$OH), 7.20-7.52 (m, 15H, C(C$_6$H$_5$)$_3$)

EXAMPLE 6

3-Hexadecyloxy-2-acetoxymethylpropan-1-ol (6)

A solution of compound 4 (2.80 g, 4.90 mmol) in acetic anhydride (5 ml) and pyridine (5 ml) was stirred at room temperature for 6 hours. The solution was concentrated and the oil was dissolved in 4:3:1 glacial acetic acid-ethanol-water (20 ml) and heated on a steam bath. After 2 hours the solution was concentrated and the residue was chromatographed on silica gel using 10% ethylacetatehexane to afford 1.53 g (84%) of the title compound (6) as a waxy white solid, m.p. 33°. NMR (CDCl$_3$, (CH$_3$)$_4$Si); δ0.90 (t, 3H, J=6 Hz, —CH$_3$), 1.25 (s, 26H, —CH$_2$—), 1.54 (m, 2H, —OCH$_2$CH$_2$R), 2.03 (s, 3H, CH$_3$), 2.16 (m, 1H, CH), 2.54 (t, 1H, J=6.5 Hz, —OH), 3.41 (t, 3H, J=6.5 Hz, —OCH$_2$R), 3.53, 3.56 (ABX, 2H, J$_{AB}$=8.5, /J 5 Hz, —CH$_2$OR), 3.73 (t, 2H, J=5 Hz, CH$_2$OH), 4.18 (d, 2H, J=6.5 Hz, CH$_2$OAc).

EXAMPLE 7

1-Hexadecyl-2-acetyloxymethylglycerol (7)

The title compound (7) was obtained following the same procedure as in Example 6 but using compound 5 in place of compound 4, 90% yield, m.p. 44° C. NMR (CDCl$_3$, (CH$_3$)$_4$Si); δ0.90 (t, 3H, J=6 Hz, —CH$_2$), 1.25 (s, 26 Hz, —CH$_2$—), 1.56 (t, 2H, J=6 Hz, —OCH$_2$CH$_2$R), 2.11 (s, 3H, —CH$_3$), 2.48 (t, 1H, J=6 Hz, —OH), 2.96 (s, 1H, —OH), 3.48 (t, 4H, J=7 Hz), 3.61 (d, 2H, J=6.5 Hz), 4.16 (s, 3H, CH$_2$OAc).

EXAMPLE 8

2-Hexadecyloxymethyl-2-propen-1-ol (8)

A solution of compound 2 (0.714 g, 1.29 mmol) in 8 ml of 4:3:1 glacial acetic acid-ethanolwater was heated on a steam bath for 2 hours. The solution was cooled and concentrated and the residue was chromatographed on silica gel using 20% ethylacetate-hexane to afford 0.314 g (78%) of the title compound (8) as a waxy solid, m.p. 34°. NMR (CDCl$_3$, (CH$_3$)$_4$Si); δ0.90 (t, 3H, J=6 Hz, CH$_3$), 1.29 (s, 26H, —CH$_2$—), 1.60 (m, 2H, —OCH$_2$CH$_2$R), 2.0 (t, 1H, J=6 Hz, —OH), 3.44 (t, 2H, J=7 Hz, —OCH$_2$R), 4.04 (s, 2H, —CH$_2$OR), 4.19 (d, 2H, J=6 Hz, CH$_2$OH), 5.07 (d, 1H, J=1Hz, olefin), 5.12 (d, 1H, J=1 Hz, olefin).

EXAMPLE 9

1-Hexadecyloxy-2-methanesulfonyloxymethyl-3-triphenylmethoxypropane (9)

Methanesulfonylchloride (0.752 g, 6.57 mmol) was added to a solution of 4 (3.00 g, 5.26 mmol) in dry pyridine (15 ml). After 3 hours the solution was poured into ice water and the product was extracted 3 times with hexane. The hexane extracts were washed with cold 1M H saturated NaHCO$_3$ and water, and dried over Na$_2$SO$_4$ and concentrated. Chromatography on silica gel using hexane-CH$_2$Cl$_2$ (1:1 v/v) afforded 3.40 g (99%) the title compound (9) as a waxy solid, m.p. 39°. NMR (CDCl$_3$, (CH$_3$)$_4$Si); δ0.90 (t, 3H, J=6 Hz, —CH$_3$), 1.25 (s, 26H, —CH$_2$—), 1.52 (m, 2H, OCH$_2$CH$_2$R), 2.28 (m, 1H, CH), 2.84 (s, 3H, —CH$_3$), 3.19, 3.21 (ABX, 2H, J$_{AB}$=10 Hz, /J$_{AX}$+J$_{BX}$/=8 Hz, CH$_2$OTr, 3.35 (t, 2H, J=6.5 Hz, —OCH$_2$R), 3.48 (d, 2H, J=6 Hz, CH$_2$OR), 4.39 (d, 2H, J=6 Hz, CH$_2$OMs).

EXAMPLE 10

1-Hexadecyloxy-2-fluoromethyl-3-triphenylmethoxypropan (10)

A solution of 9 (1.10 g, 1.70 mmol) and tetrabutylammonium fluoride (2.00 g, 7.60 mmol) in dry N,N-dimethylformamide was stirred under N$_2$ at 60°. After 18 hours, the solution was concentrated and the residue was partitioned between hexane and water. The hexane layer was washed 3 times with water, dried over Na$_2$SO$_4$ and concentrated. Chromatography on silica gel using hexane-CH$_2$Cl$_2$ (1:1, v/v) afforded 0.871 g (87%) of the title compound (10) as a colorless wax, m.p. 32°. NMR (CDCl$_3$, —(CH$_3$)$_4$Si); δ0.90 (t, 3H, J=6 Hz, —CH$_3$), 1.25 (s, 26H, —CH$_2$—), 1.55 (m, 2H, —OCH$_2$CH$_2$R), 2.32 (d of septets, 1H, J$_{H-H}$=6 Hz, J$_{H-F}$=23.5 Hz, —CH), 3.19 (d, 2H, J=6.0 Hz, —CH$_2$OTr), 3.36 (t, 2H, J=6.5 Hz, —OCH$_2$R), 3.49 (d, 2H, J=6.0 Hz, —CH$_2$OR), 4.59 (d of d, 2H, J$_{HH}$=6.0 Hz, J$_{H-F}$=47.5 Hz, —CH$_2$F), 7.2-7.52 (m, 15H, —C(C$_6$H$_5$)$_3$)

EXAMPLE 11

3-Hexadecyloxy-2-fluoromethyl-1-propanol (11)

A solution of 0.750 g (123 mmol) of 10 in 5 ml glacial acetic acid was cooled to 0°. To this was added 2 ml of HBr-acetic acid and the mixture was stirred at 0° for 45 seconds. The solution was filtered and the filtrate was poured into ice water and the mixture was partitioned between methylene chloride and water. The aqueous layer was washed with two portions of methylene chloride and the organic extracts were washed with aqueous $Na_2CO_3$ and water, dried over $Na_2SO_4$, and concentrated. The residue was chromatographed on silica gel using hexane-ethyl acetate eluent (9:1, v/v) to afford 0.388 g (88%) of the title compound (11) as a colorless wax, m.p. 34°. NMR ($CDCl_3$, $(CH_3)_4Si$); δ 0.90 (t, 3H, J=6 Hz), 1.25 (s, br, 26H), 1.59 (m, 2H), 2.10 (s, br, —OH), 2.19 (d of septets, 1H, $J_{H-H}$=6 Hz, $J_{H-F}$=21 Hz), 3.45 (t, 2H, J=6.5 Hz), 3.63 (d, 2H, J=6 Hz), 3.85 (d, 2H, J=6 Hz, C$\underline{H}_2$OH), 4.64 (d of d, 2H, $J_{H-H}$=6 Hz, JH-F=47 Hz).

EXAMPLE 12

3-O-Hexadecyl-2-methylglycero-1-phosphorylcholine (12)

A solution of 0.300 g (0.907 mmmol) of 3, 0.165 g (1.15 mmol) of 2-chloro-2-oxo-1,3,2-dioxaphosphorane and 0.2 ml triethylamine in 4 ml toluene was stirred for 90 minutes at room temperature. The mixture was filtered and the filtrate was concentrated to an oil that was dissolved in 5 ml of dry acetonitrile. Trimethylamine was bubbled into the solution for 10 minutes and then the flask was sealed and heated at 65° C. for 18 hours. The solution was cooled and concentrated and the residue was chromatographed on silica gel using a 60:40:10 chloroform-methanol-water eluent to afford 0.240 g (53%) of the title compound (12) as a colorless wax. NMR ($CDCl_3$-$CD_3OD$, $(CH_3)_4Si$); δ 0.90 (t, 3H, J=6 Hz), 1.18 (s, 3H, —CH$_3$), 1.26 (s, br, 26H), 1.55 (m, br, 2H), 3.30 (s, 9H, N(CH$_3$)$_3$), 3.42 (m, 2H), 3.80 (m, H), 4.04 (s, br, 2H), 4.35 (s, br, 2H).

EXAMPLE 13

2-Hexadecyloxymethyl-2-propene-1-phosphorylcholine (13)

The title compound was obtained following the same procedure as in Example 12 except that compound 8 was used in place of compound 3. NMR ($CDCl_3$, $CD_22D$, $(CH_3)_4Si$); δ 0.90 (t, 3H, J=7), 1.25 (s, 26H), 1.55 (m, 3H, B—CH$_2$), 3.36 (s, 9H, —N(CH$_3$)$_3$), 3.41 (t, 2H, —OCH$_2$R, J=7), 3.77 (s, H, br, C$\underline{H}_2$NMe$_3$), 3.98 (s, 2H, C$\underline{H}_2$OR), 4.30 (s, br, H, —P—OC$\underline{H}_2$CH$_2$—), 4.39 (d, 2H, CH$_2$OP—, J=6.5 Hz), 5.10 (s, H), 5.24 (s, 1H).

EXAMPLE 14

2-Acetoxymethyl-2-deoxy-3-O-hexadecylglycero-1-phosphocholine (14)

The title compound was prepared using the same procedure as in Example 13 except that compound 6 was used in place of compound 8. NMR ($CDCl_3$, $CD_3OD$, $(CH_3)_4Si$); δ 0.88 (t, 3H, —CH$_3$), 1.25 (s, 26H), 1.56 (m, 2H), 2.06 (s, 3H, CH$_3$CO), 2.28 (septet, 1H, C$\underline{H}$), 3.45 (s, 9H, N(CH$_3$)$_3$), 3.48 (m, H), 3.84 (s, br, C$\underline{H}_2$OP), 4.00 (m, 2H, C$\underline{H}_2$N), 4.32 (m, 2H, C$\underline{H}_2$OAc), 4.40 (s, br, 1H, CH$_2$OP).

EXAMPLE 15

2-Acetoxymethyl-3-O-hexadecylglycero-1-phosphocholine (15)

The title compound was prepared using the same procedure as in Example 13 except that compound 7 was used in place of compound 8. NMR ($CDCl_3$, $CD_3OD$, $(CH_3)_4Si$); δ 0.88 (t, 3H, —CH$_3$, J=7.5 Hz), 1.25 (s, 26H), 1.56 (m, 2H), 2.12 (s, 3H, C$\underline{H}_3$CO), 3.45 (s, 9H, N(CH$_3$)$_3$), 3.49 (m, 4H), 3.90 (s, br, CH$_2$OP), 4.01 (m, 2H, CH$_2$N), 4.34 (m, 2H, CH$_2$OAc), 4.45 (s, br, 1H, —POC$\underline{H}_2$).

EXAMPLE 16

2-Deoxy-2-fluoromethyl-3-0-hexadecylglycero-1-phosphocholine (16)

The title compound was prepared using the same procedure as in Example 13 except that compound 11 was used in place of compound 8. NMR ($CDCl_3$, $CD_3OD$, $(CH_3)_4Si$); δ 0.88 (t, 3H, —CH$_3$, J=7.5 Hz), 1.25 (s, 26H), 1.56 (m, 2H), 2.29 (d of septets, 1H, $J_{H-F}$=24 Hz, —CH), 3.40 (s, 9H, N(CH$_3$)$_3$), 3.52 (m, 4H), 3.80 (s, br, CH$_2$OP), 4.01 (m, 2H, CH$_2$N), 4.36 (s, 2H, —POCH$_2$), 4.60 (d of d, 2H, —CH$_2$F, $J_{H-H}$=5 Hz, $J_{H-F}$=46 Hz).

EXAMPLE 17

2-Hydroxymethyl-2-deoxy-3-O-hexadecylglycero-1-phosphocholine (17)

A solution of 0.100 g (0.186 mmol) of compound 14 and 0.010 g (0.185 mmol) NaOCH$_3$ in 5 ml methanol as stirred at room temperature for 6 hours. The solution was neutralized with 5 ml AG 1×2 (H+form) and the resin was removed by filtration and washed with 100 ml 5% pyridine in methanol. The combined washings were concentrated to afford 0.071 g (77%) of the title compound (17) as a colorless glass. NMR ($CDCl_3$, —CD$_3$OD, $(CH_3)_4Si$); δ 0.88 (t, 3H, J=7.5 Hz), 1.25 (s, 26H), 1.56 (m, 2H, OCH$_2$C$\underline{H}_2$), 2.10 (septet, 1H, CH), 3.40 (m, 4H), 3.45 (s, 9H, N(C$\underline{H}_3$)$_3$), 3.61 (m, 2H, C$\underline{H}_2$OP), 3.72 (m, 2H), 3.96 (m, 2H, C$\underline{H}_2$N), 4.28 (s, br, 1H, OPOCH$_2$).

EXAMPLE 18

2-Hydroxymethyl-3-O-hexadecylglycero-1-phosphocholine (18)

The title compound was prepared using the same procedure as in Example 17 except that compound 15 was used in place of compound 14. NMR ($CDCl_3$, —CD$_3$OD, $(CH_3)_4Si$); δ 0.90 (t, 3H, —CH$_3$, J=7.5 Hz), 1.25 (s, 26H), 1.60 (m, 2H), 3.40 (m, 4H), 3.45 (s, 9H, N(CH$_3$)$_3$), 3.65 (m, 2H, CH$_2$OP), 3.70 (m, 2H), 4.00 (m, 2H, C$\underline{H}_2$N), 4.40 (s, br, 1H, —POCH$_2$).

REACTION SCHEME II, EXAMPLES 19–36

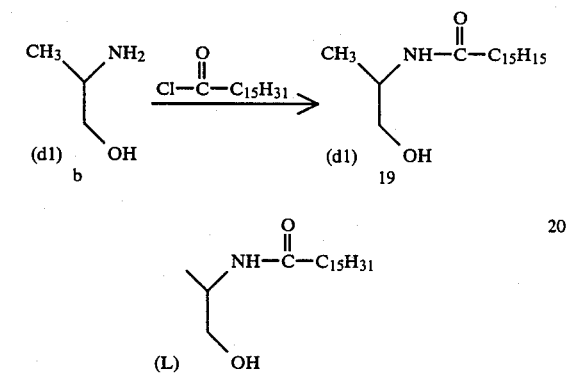

-continued
REACTION SCHEME II, EXAMPLES 19-36
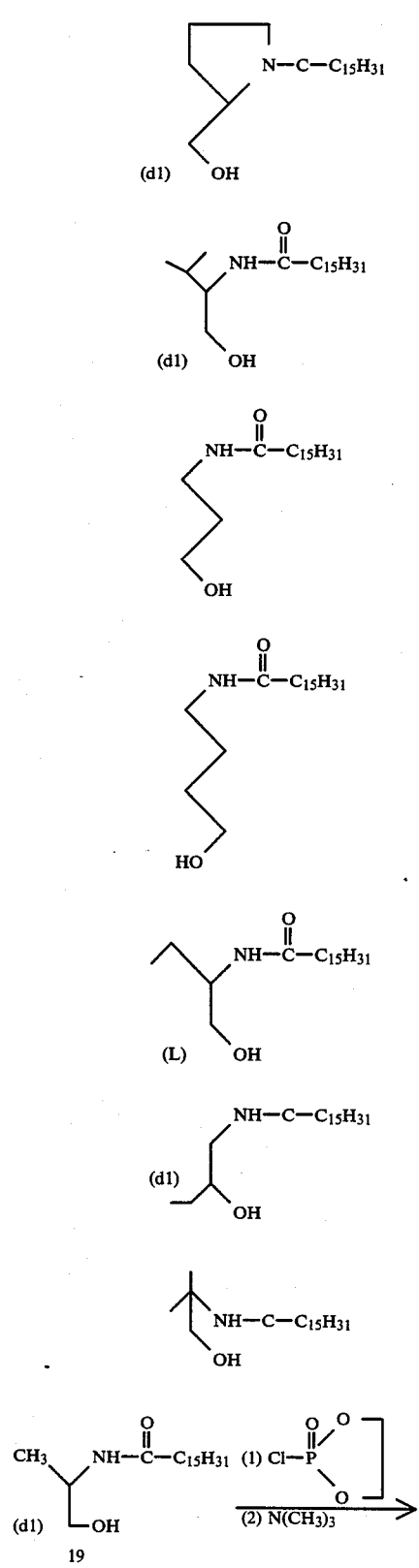
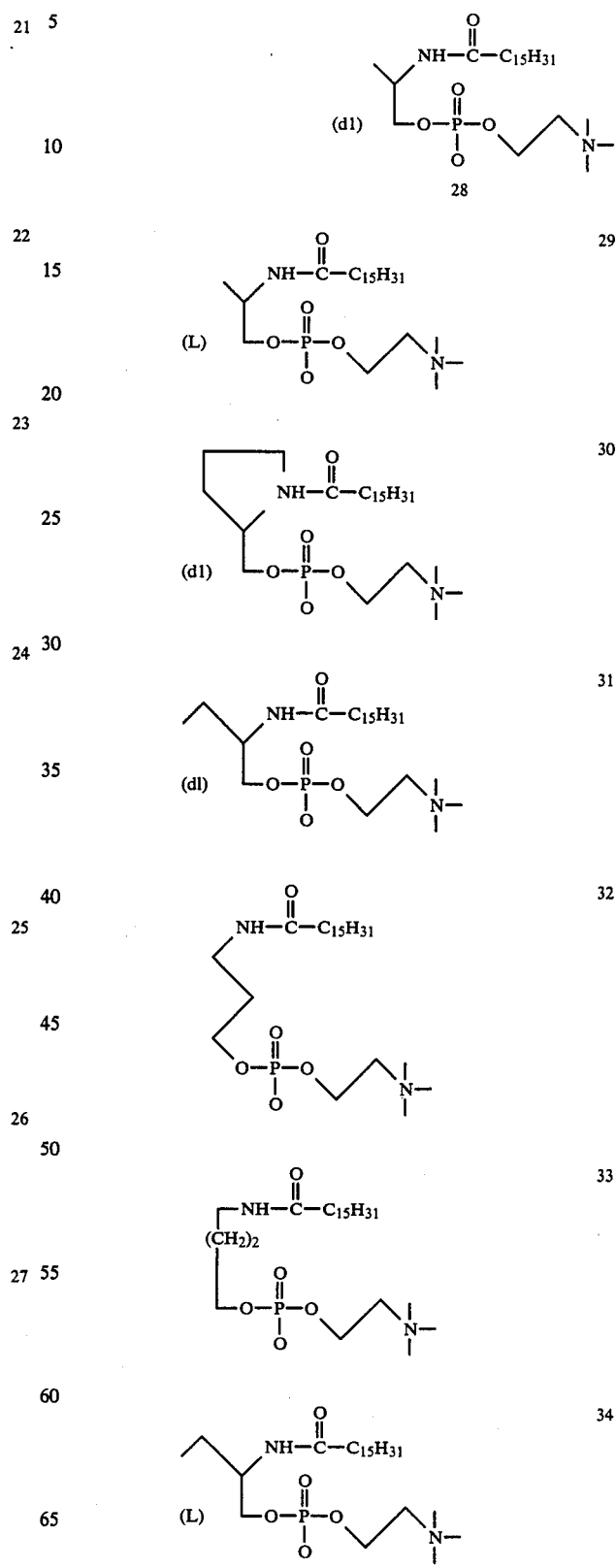

-continued
REACTION SCHEME II, EXAMPLES 19-36

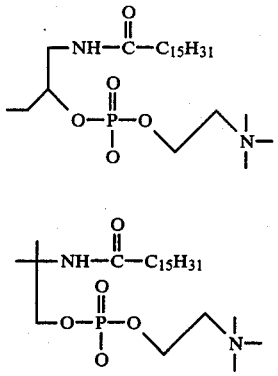

EXAMPLE 19 dl-2-(N-Hexadecanoyl)amino-1-propanol (19)

A solution of 4.00 g (53.2 mmol) of commercially obtained dl-2-amino-1-propanol b and 8.0 g (8.8 ml, 29.3 mmol) of hexadecanoyl chloride in 100 ml of $CH_2Cl_2$ was stirred at room temperature for hours. The solution was concentrated and the residue was boiled with 200 ml acetone and decanted. The solution was concentrated and the residue was chromatographed on silica gel using 50% ethylacetate in hexane to afford 4.15 g (51%) of the title compound as white needles, m.p. 75-76° C. Using the same procedure as in Example 19, the following compounds were prepared:

EXAMPLE 20

L-2-(N-Hexadecanoyl)amino-1-propanol (20)

63% yield, m.p. 84-85° C.

EXAMPLE 21 dl-1-N-Hexadecanoyl-2-hydroxymethylpyrrolidine (21)

53% yield, m.p. 37-38° C.

EXAMPLE 22 dl-2-(N-Hexadecanoyl)amino-3-methyl-1-butanol (22)

73% yield, m.p. 74-75° C.

EXAMPLE 23

3-Hexadecanoylaminopropane-1-ol (23)

92% yield, m.p. 92° C.

EXAMPLE 24

4-Hexadecanoylaminobutane-1-ol (24)

m.p. 102° C.

EXAMPLE 25

2-Hexadecanoylamino-L-butane-1-ol (25)

m.p. 95°-96° C.

EXAMPLE 26

1-Hexadecanoylaminobutane-2-ol (26)

m.p. 79°-79.5° C.

EXAMPLE 27

2-Hexadecanoylamino-2-methylpropane-1-ol (27)

m.p. 60°-61° C.

EXAMPLE 28

(dl-2-N-Hexadecanoylamino)-1-propoxyphosphorylcholine (28)

A mixture of 1.00 g (3.19 mmol) of compound 19 and 0.45 ml (3.19 mmol) of triethylamine in 5 ml of dry toluene was warmed on a steam bath until the solid dissolved. Then 0.455 g (3.19 mmol) of 2-chloro-2-oxo-1,3,2-dioxaphosphorane was added and the solution was stirred at room temperature for 2 hours.

The solution was warmed and filtered and the filtrate ws concentrated. The residue was dissolved in dry acetonitrile and 1 ml of trimethylamine was added. The flask was sealed and heated at 65° C. for 18 hours. Then the mixture was cooled and filtered and the residue chromatographed on silica gel using 1:9:1 $CHCl_3$-methanol 30% $NH_4OH$ to afford 0.389 g (25%) of the title compound (28) as a white powder, NMR ($CDCl_3$, $CD_3OD$, $(CH_3)_4Si$); δ0.89 (3H, t, $CH_3$), 1.16 (d, 3H, J=6.5 Hz), 1.25 (s, 24H), 1.61 (m, 2H, —$CH_2$), 2.17 (t, 2H, —$CH_2$—, J=7.5 Hz), 3.24 (s, 9H, $(CH_3)_3$—N—), 3.65 (s, br, 2H, $CH_2NMe_3$), 3.82 (m, br, 2H, $CH_2OP$), 4.08 (m, 1H, $CHCH_3$), 4.26 (s, br, 2H, $POCH_2$).

Using the same procedure as in Example 28, the following compounds were prepared:

EXAMPLE 29 dl-2-N-Hexadecanoylamino-1-propoxyphosphorylcholine (29)

27% NMR ($CDCl_3$, $CD_3OD$, $(CH_3)_4Si$); δ0.89 (3H, t, $CH_3$), 1.16 (d, 3H, J-6.5 Hz, $CH_3CH$), 1.25 (s, 24H), 1.61 (m, 2H, —$CH_2$), 2.17 (t, 2H, J=7.5 Hz, —$CH_2$—), 3.24 (s, 9H, $(CH_3)_3N$—), 3.65 (s, br, 2H, $CH_2NMe_3$), 3.82 (m, br, 2H, $CH_2OP$), 4.08 (m, 1H, $CHCH_3$), 4.26 (s, br, 2H, $POCH_2$).

EXAMPLE 30

N-Hexadecanoylpyrrolidin-2-yl-methyloxyphosphorylcholine (30)

NMR ($CDCl_3$—$DC_3OD$, $(CH_3)_4Si$) δ0.88 (t, 3H, —$CH_3$), 1.25 (s, br, 24 H), 1.61 (m, 2H), 1.89 (m, 2H), 2.08 (m, 2H), 2.19 (t, 2H, $CH_2CON$), 3.40 (s, 9H, $(CH_3)_3N$), 3.50 (m, 2H), 3.85 (s, br, 2H, $CH_2OP$), 3.98 (m, 2H, $CH_2N$), 4.10 (m, 1H), 4.38 (s, br, 2H, $POCH_2$).

EXAMPLE 31

2-N-Hexadecanoylamino-3-methyl-1-propoxyphosphorylcholine (31)

NMR ($CDCl_3$—$CD_3OD$ $(CH_3)_4Si$) δ0.89 (m, 9H, $CH_3$), 1.25 (s, br, 24 H), 1.60 (m, 2H), 1.85 (septet, 1H, $CH$), 2.20 (m, 2H, $CH_2CO$), 3.35 (s, 9H, $(CH_3)_3N$), 3.70 (s, br, 2H, $CH_2OP$), 3.95 (m, 2H, $CH_2N$), 4.32 (s, 2H, $POCH_2$).

EXAMPLE 32

3-N-Hexadecanoylamino-1-propoxyphosphorylcholine (32)

NMR ($CDCl_3$—$CD_3OD$): δ0.89 (t, 3H, $CH_3$), 1.61 (m, 2H, $\beta CH_2$), 1.80 (m, 2H, C—$CH_2$—C), 2.19 (t, 2H, $\alpha CH_2$, J=7.5 Hz), 3.26 (S, 9H, $NMe_3$), 3.34 (t, 2H, $CH_2NHCO$, J=6.0 Hz), 3.67 (m, 2H, $CH_2N^+Me_3$), 3.96

(q, 2H, CH$_2$OPO$_3$, J=6.0 Hz, 12.0 Hz), 4.28 (b, 2H, PO$_3$CH$_2$).

EXAMPLE 33

4-N-Hexadecanoylamino-1-butyloxyphosphorylcholine (33)

NMR was in accord with the structure.

EXAMPLE 34

L-2-N-Hexadecanoylamino-1-butyloxyphosphorylcholine (34)

NMR (CDCl$_3$): δ0.94 (t, 3H, CH$_3$), 1.63 (m, 2H, βCH$_2$), 2.20 (m, 2H, αCCH$_2$), 3.24 (s, 9H, N+Me$_3$), 3.64 (b, 2H, CH$_2$N+Me$_3$), 3.90 (m, 2H, CH$_2$OPO$_3$), 4.28 (m, 2H, PO$_3$CH$_2$).

EXAMPLE 35 dl-1-N-Hexadecanoylamino-2-butyloxyphosphorylcholine (35)

NMR was in accord with the structure.

EXAMPLE 36

2-N-Hexadecanoylamino-2-methyl-1-propyloxyphosphorylcholine (36)

NMR (CDCl$_3$): δ0.88 (t, 3H, CH$_3$), 1.57 (b, 2H, βCH$_2$), 2.11 (t, 2H, αCH$_2$), 3.26 (s, 9H, N+Me$_3$), 4.64 (b, 2H, CH$_2$N+Me$_3$), 3.83 (d, 2H, CH$_2$OPO$_3$), 4.25 (m, 2H, PO$_3$CH$_2$).

REACTION SCHEME III, EXAMPLES 37–44

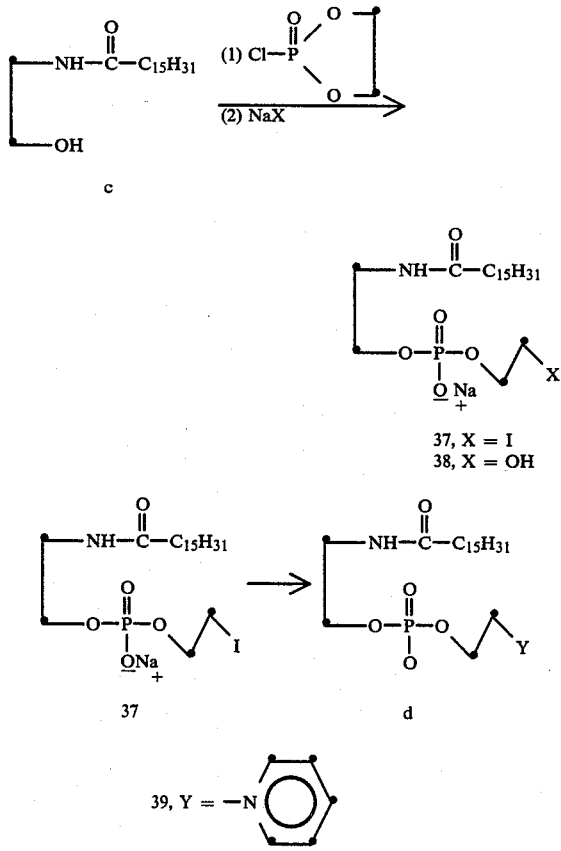

-continued
REACTION SCHEME III, EXAMPLES 37–44

40, Y = —N⟨   ⟩O⁻ Na⁺

41, Y = N$_3$ Na⁺

42, Y = N(CH$_3$)$_2$ Na⁺

43, Y = —NH$_2$ Na⁺

44, Y = —SCH$_3$ Na⁺

EXAMPLE 37

Sodium 2-(2-N-hexadecanoylaminoethyl)-2'-(2-iodoethyl)phosphate (37)

A mixture of 3.00 g (10.0 mmol) of 2-N-hexadecanoylaminoethanol (c) [J. Hajdu, et al., *Biochemica et Biophysica Acta*, 711, 357–360 (1982)], 1.53 ml (12.5 mmol) of triethylamine and 1.56 g (10.9 mmol) of 2-chloro-2-oxo-1,3,2-dioxaphosphorane in 10 ml of dry toluene. It was stirred at 50° C. for 2 hours. The solution was filtered and the filtrate was concentrated. The residue was dissolved in 20 ml of dry acetone and this was heated with 5.0 g (33.3 mmol) of NaI at reflux for 3 hours. The solution was cooled and the residue was chromatographed on silica gel using 80:20:2, CHCl$_3$-methanol-water, to afford 3.16 g (57%) of the title compound as a white solid. m.p.

NMR (CDCl$_3$CD$_3$OD, (CH$_3$)$_4$Si); δ0.89 (t, 3H, —CH$_3$), 1.24 (s, 24H), 1.60 (m, 2H), 2.18 (t, 2H), 3.32 (t, 2H), 3.46 (m, 2H), 3.92 (m, 2H), 4.04 (m, 2H).

EXAMPLE 38

Sodium 2-(2-N-hexadecanoylaminoethyl)-2'-(2-hydroxyethylphosphate (38)

A mixture of 0.074 g (0.247 mmol) of 2-N-hexadecanoylaminoethane 35 μl (0.251 mmol) of triethylamine and 0.035 g (0.250 mmol) of 2-chloro-2-oxo-1,3,2-dioxaphosphorane in 1 ml of dry toluene was stirred at 50° C. for 2 hours. The solution was filtered and the filtrate was concentrated. The residue was dissolved in a mixture of 1 ml CHCl$_3$ and 1 ml of 2.5M NaOH and the 2-phase mixture was stirred rapidly at 60° C. After 24 hours, the solvents were evaporated and the residue chromatographed on silica gel using 80:20:2 CHCl$_3$-methanol-water to afford 0.72 g, (95%) of the title compound as a white powder. NMR (CDCl$_3$—CD$_3$OD, (CH$_3$)$_4$Si) δ0.88 (s, 3H, CH$_3$), 1.23 (s, 24H), 1.60 (m, 2H), 2.20 (t, 2H, J=5 Hz), 3.40 (m, 2H), 3.70 (m, 2H), 3.93 (m, 4H, CH$_2$OPOCH$_2$).

EXAMPLE 39

2-(2-N-Hexadecanoylaminoethyl-2'-(2-N-pyridiniumethyl)phosphate (39)

A solution of 0.500 g (0.904 mmol) of compound 37 and 5 ml pyridine in 5 ml CHCl$_3$ was sealed and heated at 110° C. for 18 hours. The solution was concentrated and the residue was chromatographed on silica gel using 1:9:1 CHCl$_3$-methanol-water to afford 0.33 g (75%) of the title compound as a white powder.

NMR (CDCl₃—CD₃OD, (CH₃)₄Si) δ0.89 (t, 3H, —CH₃), 1.25 (s, 24H), 1.61 (m, 2H), 2.18 (t, 2H, J=7.5 Hz), 3.85 (m, 2H, CH₂OP), 4.30 (s, br, CH₂OP), 4.84 (s, br, —CH₂—N).

EXAMPLE 40

Sodium 2-(2-N-hexadecanoylaminoethyl)-2-(2-N-morpholinoethyl)phosphate (40)

The title compound was prepared as in Example 39 except that morpholine was used instead of pyridine to afford 71% of a colorless glass. NMR (CDCl₃), (CH₃)₄Si) δ0.89 (t, 3H, CH₃), 1.25 (s, 24H), 1.60 (m, 2H), 2.19 (t, 2H, J=7.5 Hz), 2.89 (m, 6H), 3.50 (m, 2H), 3.89 (m, 4H), 3.96 (m, 2H, CH₂OP), 4.10 (m, 2H, POCH₂).

EXAMPLE 41

Sodium 2-(2-N-hexadecanoylaminoethyl)-2'-(2-azidoethyl)phosphate (41)

A solution of 4.05 g (7.30 mmol) of compound 37 and 3.05 g (46.9 mmol) of sodium azide in 20 ml of N,N-dimethylformamide was heated at 65° for 3 hours. The solution was concentrated and the residue was chromatographed on silica gel using 80:20:2 chloroform-methanol-water to afford 1.81 g (51%) of the title compound (59) as a white powder. IR—2130 cm. NMR (CDCl₃—CD₃OD, (CH₃)₄Si); δ0.89 (t, 3H, —CH₃), 1.25 (s, 24H), 1.63 (m, 2H, —CH₂), 2.19 (t, 3H, —CH₂—, J=7.5 Hz), 3.50 (m, 4H), 3.98 (m, 2H, CH₂OP), 4.23 (s, br, 2H, CH₂OP).

EXAMPLE 42

Sodium 2-(2-N-hexadecanoylaminoethyl)-2'-(2-N,N-dimethylaminoethyl)phosphate (42)

The title compound was prepared as in Example 41 except that dimethylamine in acetonitrile was used instead of sodium azide in DMF to afford 70% of a colorless wax. NMR (CDCl₃, (CH₃)₄Si) δ 0.88 (t, 3H), 1.25 (s, 24H), 1.61 (m, 2H), 2.19 (t, 2H, —CH₂—, J=7.5 Hz), 2.90 (s, 6H, N(CH₃)₂), 3.26 (s, br, CH₂NMe₂), 3.47 (t, 2H, CH₂NCOR, J=5.0 Hz), 3.98 (m, CH₂OP), 4.23 (s, br, POCH₂—).

EXAMPLE 43

Sodium 2-(2-N-hexadecanoylaminoethyl)-2'-(2-aminoethyl)phosphate (43)

The title compound was prepared as in Example 41 except that ammonia in chloroform was used instead of sodium azide in dimethylformamide to afford 91% of a white glass. NMR (CDCl₃—CD₃OD, (CH₃)₄Si) δ0.88 (t, 3H), 1.24 (s, 24H), 1.61 (m, 2H), 2.20 (t, 2H, —CH₂—, J=7.5 Hz), 3.26, (s, br, CH₂NH₂), 3.48 (t, 2H, CH₂NCOR, J=5.0 Hz), 3.98 (m, CH₂OP), 4.25 (s, br, POCH₂—).

EXAMPLE 44

Sodium 2-(2-N-hexadecanoylaminoethyl)-2'-(2-methylthioethyl)phosphate (44)

The title compound was prepared as in Example 41 except that sodium methyl mercaptide was used instead of sodium azide to afford 92% of a pale yellow solid. NMR (CDCl₃—CD₃OD, (CH₃)₄Si); δ0.89 (t, 3H), 1.26 (s, 24H), 1.63 (m, 2H), 2.19 (m, 3H, SCH₃), 2.52 (s, 3H, CH₃S), 2.78 (t, 2H, CH₂S), 3.51 (m, 2H, CH₂N), 4.00 (m, 4H, CH₂OPOCH₂).

REACTION SCHEME IV, EXAMPLES 45-47

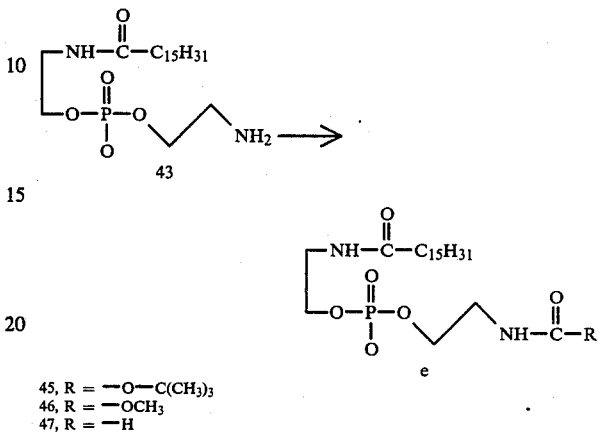

45, R = —O—C(CH₃)₃
46, R = —OCH₃
47, R = —H

EXAMPLE 45

Sodium 2-(2-N-hexadecanoylaminoethyl)-2'-[t-butyloxy)carbonylaminoethyl]phosphate (45)

A solution of 0.100 g (0.225 mmol) of 43 and 0.249 g (1.27 mmol) of di-t-butoxycarbonyldicarbonate in 1 ml of N,N-dimethylformamide was stirred at room temperature for 30 hours. The solution was concentrated and the residue triturated with acetone to afford 0.094 g (76%) of the title compound (45) as a white powder. NMR (CDCl₃—CD₃OD₃, (CH₃)₄Si); δ0.88 (t, 3H, —CH₃, J=7.5 Hz), 1.26 (s, 24H), 1.36 (s, 9H, C(CH₃)₃), 1.60 (m, 2H), 2.18 (t, 2H, J=5 Hz), 3.10 (m, 2H, CH₂N), 3.44 (m, 2H, CH₂NCOR), 3.95 (m, 2H, CH₂OP), 4.20 (m, 2H, POCH₂).

EXAMPLE 46

Sodium 2-(2-N-hexadecanoylaminoethyl)-2'-(2-methylcarbonylaminoethyl)phosphate (46)

To a suspension of 0.100 g (0.225 mmol) of 43 and 500 mg Na₂CO₃ in 5 ml CHCl₃ was added 100 μl of methylchloroformate. The mixture was stirred at room temperature for 18 hours, then was filtered and evaporated. The residue was chromatographed on silica gel using 80:20:2 chloroform-methanol water to afford 0.081 g (71%) of the title compound (46) as a colorless glass. NMR (CDCl₃—CD₃OD, (CH₃)₄Si); δ0.90 (t, 3H, —CH₃, J=7.5 Hz), 1.25 (s, 24H), 1.63 (m, 2H), 2.20 (t, 2H), 3.42 (m, 4H), 3.68 (s, 3H, OCH₃), 4.06 (m, 4H, POCH₂).

EXAMPLE 47

Sodium 2-(2-N-hexadecanoylaminoethyl)-2'-(2-N-formylaminoethyl)phosphate (47)

The title compound was prepared as in Example 46 except that formylacetate was used instead of methylchloroformate to afford 0.073 g (69%) of a colorless solid. NMR (CDCl₃—CD₃OD, (CH₃)₄Si); δ0.88 (t, 3H, —CH₃, J=7.5 Hz), 1.26 (s, 24H), 1.65 (m, 2H), 2.20 (t, 2H), 3.40 (m, 4H), 3.85 (m, 4H, POCH$_2$), 8.15 (s, 1H, NCHO).

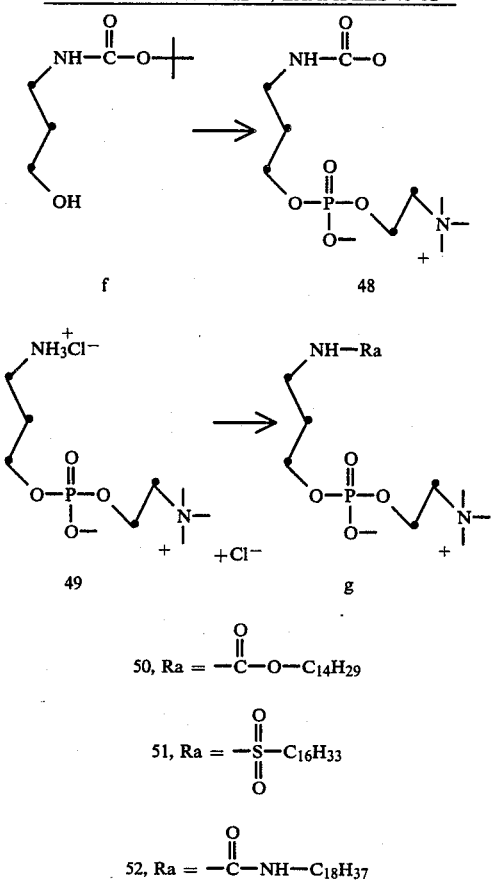

REACTION SCHEME V, EXAMPLES 48-52

50, Ra = $-\overset{O}{\underset{\|}{C}}-O-C_{14}H_{29}$

51, Ra = $-\overset{O}{\underset{\underset{\|}{O}}{\overset{\|}{S}}}-C_{16}H_{33}$ 52, Ra = $-\overset{O}{\underset{\|}{C}}-NH-C_{18}H_{37}$

EXAMPLE 48

3-(t-Butyloxycarbonylamino)propyloxyphosphorylcholine (48)

The title compound was prepared as in Example 28 except that 3-(t-butyloxycarbonylamino) propanol [G. Zimmer, et al., *Arch. Pharm.*, 302, 916–920 (1969)] was used instead of 2-hexadecanoylamino-1-propanol to afford 1.43 g (73%) of a colorless foam NMR (CDCl$_3$—CD$_3$OD, (CH$_3$)$_4$Si). δ1.42 (s, 9H, C(CH$_3$)$_3$), 1.78 (m, 2H), 3.42 (m, 2H), 3.48 (s, 9H, (CH$_3$)$_3$N), 3.80 (m, 2H, CH$_2$OP), 3.98 (m, 2H, —N—CH$_2$), 4.26 (s, br, POCH$_2$).

EXAMPLE 49

3-Aminopropyloxyphosphorylcholine dihydrochloride (49)

To a solution of 0.200 g (0.586 mmol) of 48 in 2 ml of chloroform was added 1 ml of HCl-saturated ether. The solution was shaken at room temperature for 20 minutes then concentrated to afford 0.190 g (96%) of the title compound as a colorless glass.

Anal.: Calc'd: N, 8.95; C, 30.61; H, 7.40; P, 9.90; Cl, 22.64.
Found: N, 8.59; N, 30.26; H, 7.46; P, 10.49; Cl, 20.37.

EXAMPLE 50

3-Tetradecycloxycarbonylaminopropyl-2-phosphorylcholine (50)

A mixture of 1-aminopropyl-3-phosphorylcholine hydrochloride (270 mg) and p-nitrophenyltetradecylcarbonate (380 mg) in DMF (10 ml) and isopropanol (10 ml) was stirred at room temperature for 2 days. The solution was evaporated in vacuo to a residue which was put on a column of silica gel and eluted with CHCl$_3$—MeOH—H$_2$O (5:5:1, v/v). The title compound was isolated as a foam (260 mg), MS, m/z 481 (M$^+$+1).

EXAMPLE 51

3-Hexadecylsulfonaminopropyl-1-phosphorylcholine (51)

A solution of 1-hexadecanesulfonylchloride (800 mg, 2.5 mmol) in acetone (10 ml) was added dropwise to a solution of 1-aminopropyl-3-phosphorylcholine hydrochloride (670 mg, 2.4 mmol) in water (5 ml) containing sodium carbonate (600 mg) at 0°. The mixture was stirred at room temperature for 3 hours and water was added. The product was extracted with CHCl$_3$—MeOH (9:1, v/v). The organic layer was evaporated to dryness and the residue was put on a column of silica gel eluted with CHCl$_3$—MeOH—H$_2$O (5:5:1, v/v). The title compound was isolated in low yield (100 mg), MS, m/z 528 (M$^+$+1).

EXAMPLE 52

3-Octadecylaminocarbonylaminopropyl-1-phosphorylcholine (52)

A mixture of 1-aminopropyl-3-phosphorylcholine (630 mg, 2 mmol) and octadecyl isocyanate (600 mg, 2 mmol) in methanol (10 ml) containing triethylamine (300 μl) was stirred at room temperature overnight. The solution was evaporated in vacuo and the residue was put on a column of silica gel and eluted with CHCl$_3$—MeOH—H$_2$O (1:9:1, v/v). The title compound (420 mg) gave m/z 536 (M$^+$+1) in man. spec.

REACTION SCHEME VI, EXAMPLES 53-54

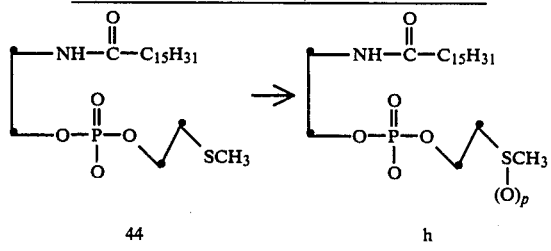

53, p = 1

54, p = 2

EXAMPLE 53

Sodium 2-(2-N-hexadecanoylaminoethyl)-2'-(2-methylsulfinylethyl)phosphate (53)

A solution of 0.250 g (0.526 mmol) of 44 and 0.091 g (0.447 mmol) of 85% m-chloroperbenzoic acid in 5 ml ethanol was stirred at 0° for 30 minutes. The solution was concentrated and the residue was chromatographed on silica using 80:20:2 chloroformmethane 30% ammonia to afford 0.165 g (75%) of a white powder. NMR (CDCl$_3$—CD$_3$OD, (CH$_3$)$_4$Si); δ0.89 (t, 3H, —CH$_3$), 1.25 (s, 24H), 1.61 (m, 2H), 2.19 (t, 2H), 2.72 (s, 3H, —OSCH$_3$), 3.01 (t, 2H, CH$_2$SO), 3.50 (t, 2H, CH$_2$N), 3.96 (s, br, 2H, CH$_2$OP), 4.10 (s, br, 2H, POCH$_2$).

EXAMPLE 54

Sodium 2-(2-N-hexadecanoylaminoethyl-2'-(2-methylsulfenylethyl)phosphate (54)

A solution of 0.250 g (0.526 mmol) of 44 and 0.250 g (1.44 mmol) of 85% m-chloroperbenzoic acid in 5 ml ethanol was stirred at 0° for 75 minutes. The solution was concentrated and the residue was chromatographed on silica gel using 80:20:2 chloroform-methanol-30% ammonia to afford 0.189 g (71%) of a white powder. NMR (CDCl$_3$—CD$_3$OD, (CH$_3$)$_4$Si); δ0.89 (t, 3H, —CH$_3$), 1.25 (s, 24H), 1.60 (m, 2H), 2.19 (t, 2H), 2.96 (s, 3H, SO$_2$CH$_3$), 3.50 (m, 4H, CH$_2$SO and CH$_2$NH), 3.98 (s, br, 2H, CH$_2$OP), 4.14 (s, br, 2H, POCH$_2$).

EXAMPLE 55

Compounds of the invention were tested for PAF biosynthesis inhibition according to the procedure of Wykle, et al. [*J. Biol. Chem.*, 255, 1056 (1980)] except for the modifications and specifications listed below:
(1) Product PAF was estimated after reaction by liquid scintillation counting of the dried chloroform phase. Controls demonstrated (by TLC) that this chloroform-soluble radioactivity was primarily PAF,
(2) [$^3$H]Acetyl Co A was used in place of [$^{14}$C],
(3) Incubation (i.e., reaction) times were generally within the range of 5–8 minutes.
(4) Concentrations used were in 1 ml of reaction mixture as follows:
Acetyl CoA ~100 μM
[$^3$H] ~0.5–4.0 μM
Lyso PAF ~5 μM
Rat spleen microisomes: 50–150 μg protein
(5) Solvents:
Water
dimethylsulfoxide (DMSO)
methanol (MeOH)
ethanol (EtOH)

The results obtained and the compounds tested are set forth in Table I below wherein "% I" represents percent inhibition and "AC$_{50}$" represents the concentration of the test compound to obtain 50% aggregation of rabbit platlets. The AC$_{50}$ results were obtained only for those compounds which are structurally similar to PAF.

TABLE I

| PAF BIOSYNTHESIS INHIBITION | | |
|---|---|---|
| Compound of Example | % I (10 μM) | AC$_{50}$ |
| 12 | 73 | >10$^{-4}$ M |
| 13 | 38 | 1.3 × 10$^{-6}$ M |
| 14 | 36 | 3.4 × 10$^{-7}$ M |
| 15 | 71 | 7 × 10$^{-8}$ M |
| 16 | 30 | 2.2 × 10$^{-6}$ M |
| 17 | 20 | 2.4 × 10$^{-5}$ M |
| 18 | 82 | 3.8 × 10$^{-5}$ M |
| 46 | 90 | |

TABLE I-continued

| PAF BIOSYNTHESIS INHIBITION | | |
|---|---|---|
| Compound of Example | % I (10 μM) | AC$_{50}$ |
| 48 | 48 | |
| 50 | 65 | |
| 51 | 34 | |
| 52 | 74 | |
| 53 | 71 | |
| 56 | 39 | |
| 57 | 40 | |
| 58 | 38 | |
| 59 | 77 | |
| 60 | 28 | |
| 61 | 26 | |
| 62 | 20 | |
| 68 | 70 | |
| 69 | 61 | |
| 70 | 55 | |

What is claimed is:

1. A method of treating disorders or diseases mediated by the PAF which comprises administering to a patient in need of such treatment of PAF biosynthesis inhibitory amount of a compound having the formula:

$$\begin{array}{c} R^1 \quad H \quad O \\ | \quad | \quad \| \\ -N-C-(CH_2)_{14}CH_3 \\ R^2 \\ (CH_2)_m \quad O \\ \quad \| \\ -O-P-O-(CH_2)_2-N(CH_3)_3^+ \\ R^3 \quad | \\ O^- \end{array}$$

wherein:
m is 0, 1 or 2;
when m is 0, R$^1$, R$^2$ and R$^3$ are as tabulated below:

| R$^1$ | R$^2$ | R$^3$ |
|---|---|---|
| H | H | CH$_2$CH$_3$ |
| CH$_3$ | CH$_3$ | H |
| CH$_3$ | H | H |
| or CH$_2$CH$_3$ | H | H | when m is 1 or 2, R$^1$, R$^2$ and R$^3$ independently are H or C$_{1-6}$ alkyl.

2. The method of claim 1 wherein the compound is of formula $$\begin{array}{c} H \quad O \\ | \quad \| \\ -N-C-(CH_2)_{14}CH_3 \\ (CH_2)_2 \\ \quad O \\ \quad \| \\ -O-P-O-(CH_2)_2-N(CH_3)_3^+ \\ \quad | \\ O^- \end{array}$$

3. The method of claim 1 wherein the compound is of formula

4. The method of claim 1 wherein the compound is of formula $$\begin{array}{c} CH_3 \\ \phantom{xx}\diagdown \\ \phantom{xxx}-N-C-(CH_2)_{14}CH_3 \\ \phantom{xxx}H \phantom{xx} O \\ \phantom{xxx}| \\ -O-P-O-(CH_2)_2-N(CH_3)_3. \\ \phantom{xxx}\| \\ \phantom{xxx}O^- \end{array}$$

5. A compound of formula:

[structure with R¹, R², (CH₂)ₘ, R³, —N(H)—C(=O)—(CH₂)₁₄CH₃, and —O—P(=O)(O⁻)—O—(CH₂)₂—N⁺(CH₃)₃]

wherein:
m is 0, 1 or 2;
when m is 0, R¹, R² and R³ are as tabulated below:

| R¹ | R² | R³ |
|---|---|---|
| H | H | CH₂CH₃ |
| CH₃ | CH₃ | H |
| CH₃ | H | H |
| or CH₂CH₃ | H | H | when m is 1 or 2, R¹, R² and R³ independently are H or C₁₋₆ alkyl.

6. A compound of claim 5 having the formula:

[structure with (CH₂)₂ linker, N(H)—C(=O)—(CH₂)₁₄CH₃, and phosphocholine group]

7. The compound of claim 5 which is

[structure with —NH—C(=O)—(CH₂)₁₄CH₃, CH₂, and phosphocholine group]

8. The compound of claim 5 which is

[structure at top of column 28 with —NH—C(=O)—(CH₂)₁₄CH₃, CH₂, and —O—P(=O)(O⁻)—O—(CH₂)₂—N⁺(CH₃)₃]

[structure with CH₃, N(H)—C(=O)—(CH₂)₁₄CH₃, and phosphocholine group]

9. A pharmaceutical composition useful for inhibiting PAF biosynthesis comprising a pharmaceutically acceptable carrier and a PAF biosynthesis inhibitory amount of a compound having the formula:

[structure with R¹, R², (CH₂)ₘ, R³, —N(H)—C(=O)—(CH₂)₁₄CH₃, and phosphocholine group]

wherein:
m is 0, 1 or 2;
when m is 0, R¹, R² and R³ are as tabulated below:

| R¹ | R² | R³ |
|---|---|---|
| H | H | CH₂CH₃ |
| CH₃ | CH₃ | H |
| CH₃ | H | H |
| or CH₂CH₃ | H | H | when m is 1 or 2, R¹, R² and R³ independently are H or C₁₋₆ alkyl.

10. The composition of claim 9 wherein the compound is of formula

[structure with (CH₂)₂, N(H)—C(=O)—(CH₂)₁₄CH₃, and phosphocholine group]

11. The composition of claim 9 wherein the compound is of formula:

[structure with CH₂, —NH—C(=O)—(CH₂)₁₄CH₃, and phosphocholine group]

12. The composition of claim 9 wherein the compound is of formula

[structure with CH₃, N(H)—C(=O)—(CH₂)₁₄CH₃, and phosphocholine group]

* * * * *